US010960166B2

(12) United States Patent
Enk (10) Patent No.: US 10,960,166 B2
(45) Date of Patent: Mar. 30, 2021

(54) ARRANGEMENT HAVING A GAS FLOW REVERSING ELEMENT AND A SWITCHABLE CONNECTION

(71) Applicant: VENTINOVA TECHNOLOGIES B.V., AR Eindhoven (NL)

(72) Inventor: Dietmar Enk, Coesfeld (DE)

(73) Assignee: Ventinova Technologies B.V., AR Eindhoven (NL)

( * ) Notice: Subject to any disclaimer, the term of this patent is extended or adjusted under 35 U.S.C. 154(b) by 240 days.

(21) Appl. No.: 15/578,322

(22) PCT Filed: May 23, 2016

(86) PCT No.: PCT/EP2016/061558
§ 371 (c)(1),
(2) Date: Nov. 30, 2017

(87) PCT Pub. No.: WO2016/193035
PCT Pub. Date: Dec. 8, 2016

(65) Prior Publication Data
US 2018/0147383 A1    May 31, 2018

(30) Foreign Application Priority Data

Jun. 1, 2015 (DE) .......................... 102015108593.3

(51) Int. Cl.
*A61M 16/08* (2006.01)
*A61M 16/04* (2006.01)
(Continued)

(52) U.S. Cl.
CPC .... *A61M 16/0858* (2014.02); *A61M 16/0003* (2014.02); *A61M 16/0012* (2014.02);
(Continued)

(58) Field of Classification Search
CPC .............. A61M 16/201; A61M 16/202; A61M 39/22–288; A61M 2205/3331; A61M 16/20–209
See application file for complete search history.

(56) References Cited

U.S. PATENT DOCUMENTS 5,669,380 A * 9/1997 Garry ................ A61M 16/0465
128/207.14
10,406,308 B2 * 9/2019 Enk .................... A61M 16/0012
(Continued)

FOREIGN PATENT DOCUMENTS

DE    102009029959    12/2010
EP         0130930     7/1986
(Continued)

*Primary Examiner* — Kendra D Carter
*Assistant Examiner* — Thao Tran
(74) *Attorney, Agent, or Firm* — Occhiuti & Rohlicek LLP (57) ABSTRACT

The present invention relates to an arrangement (1) comprising a switchable connection (2) and a gas flow reversing element (3), e.g. according to WO 2008/113752 A1, which is suitable for using a gas supply (4), in particular oxygen, which is at excess pressure in order to selectively generate a gas stream (5) from or to a line connection (6) which can be connected, in particular via a lumen (7), to an airway of a patient (8); wherein the switchable connection (2) is arranged at the branching piece (10) or at the line connection (6) and switchably connects at least one second line (15) to the first line (13), wherein the switchable connection (2) has at least two switching positions (16, 17), wherein (1) in the first switching position (16) the first line (13) is open and the second line (15) is closed, such that the gas flow (5) through the connection (2) can flow in both directions along the first line (13); (2) in the second switching position (17), if the switchable connection (2) is arranged at the branching piece (10), the second line (15) is fluidically connected, via the
(Continued)

connection (2), to the line connection (6) and in particular to the lumen (7) or, if the switchable connection (2) is arranged at the line connection (6), the second line (15) is connected to the lumen (7).

12 Claims, 4 Drawing Sheets

(51) Int. Cl.
*A61M 16/00* (2006.01)
*A61M 16/20* (2006.01)

(52) U.S. Cl.
CPC .......... *A61M 16/04* (2013.01); *A61M 16/20* (2013.01); *A61M 16/0057* (2013.01); *A61M 2016/0027* (2013.01)

(56) References Cited

U.S. PATENT DOCUMENTS

| | | | | |
|---|---|---|---|---|
| 2002/0104537 A1* | 8/2002 | Banner | ............. | A61M 16/0012 128/204.25 |
| 2008/0058720 A1* | 3/2008 | Spohn | .................... | A61M 5/007 604/140 |
| 2009/0194453 A1* | 8/2009 | Thorne, Jr. | ........... | A61J 1/2096 206/571 |
| 2010/0236551 A1* | 9/2010 | Enk | ....................... | A61M 16/00 128/204.18 |
| 2013/0206144 A1* | 8/2013 | Ahmad | ................. | A61M 16/20 128/204.23 |
| 2015/0217069 A1* | 8/2015 | Novotni | .............. | A61M 16/024 128/204.23 |
| 2015/0314101 A1* | 11/2015 | Acker | ................... | A61M 16/00 128/203.14 |
| 2016/0067432 A1* | 3/2016 | Pierre | ............... | A61M 16/0816 128/205.24 |
| 2016/0346500 A1* | 12/2016 | Howe, Jr. | ........... | A61M 16/209 |
| 2017/0274167 A1* | 9/2017 | Huddart | ............ | A61M 16/0666 |
| 2018/0071499 A1* | 3/2018 | Goto | ...................... | A61M 25/10 |
| 2018/0117271 A1* | 5/2018 | Wigforss | ............... | A61B 5/087 |

FOREIGN PATENT DOCUMENTS

| | | |
|---|---|---|
| WO | 2008113752 | 9/2008 |
| WO | 2015004229 | 1/2015 |

\* cited by examiner

ARRANGEMENT HAVING A GAS FLOW REVERSING ELEMENT AND A SWITCHABLE CONNECTION

The subject matter of the present invention relates to an arrangement having at least a switchable connector and a gas flow reversing element. An application lies in connecting such an arrangement, firstly, to a gas supply of a pressurized gas source and, secondly, to a catheter that is introducible into the airways of a patient or to a cannula (referred to in general terms as a lumen below).

Within the scope of ventilating a patient, use is normally made of a mask or a tube, by means of which the airways, sealed to the outside, are supplied with a gas or gas mixture at low pressure, in particular oxygen and air. Alternatively, however, such a gas or gas mixture also may be injected at high pressure and with a high flow rate in bursts through a thin, unblocked catheter into the airways that are open to the outside (so-called jet ventilation). These days, this method is used, in particular, in the case of diagnostic and therapeutic interventions in the area of the upper airways (endotracheal or transtracheal jet ventilation). Here, in emergency situations, this method may also be applied outside of hospitals or in inpatient situations in hospitals.

In the case of transtracheal jet ventilation, a patient can be supplied with oxygen by way of a catheter that has been introduced directly into the trachea through the skin or by way of a cannula placed thus. These (transtracheal/endotracheal) methods are constituent parts of the currently valid algorithms for managing difficult airways and, in particular, the situation in which a patient cannot be ventilated or cannot be intubated by conventional means (a so-called "cannot ventilate, cannot intubate" situation).

However, precisely jet ventilation may be potentially life-threatening in the case of inexpedient conditions. If the airways of a patient are largely obstructed, or even completely obstructed, for example as a result of swelling or bleeding, the lungs of the patient are inflated to a greater and greater extent by the injection of respiratory air. Here, there is a risk of a rupture of the lungs (a so-called barotrauma). Furthermore, the pressure increase in the rib cage may lead to a circulatory disturbance or a circulatory collapse, no less dangerous to the patient, since the blood is no longer able to flow back to the heart in sufficient quantities.

WO 2008/113752 A1 has disclosed a gas flow reversing element which can be used in the arrangement claimed here. The entire scope of this document is referred to herewith.

U.S. 61/844,746 has disclosed a further gas flow reversing element with a bypass line, which likewise can be used in the arrangement proposed here. The entire scope of this document is also referred to herewith.

The gas flow reversing elements allow, in particular, complete ventilation of a patient (i.e. sufficient amounts of respiratory air can be supplied and used respiratory air can be discharged again—normoventilation) for an unlimited period of time. Here, the gas flow passes through a single lumen in both directions (toward and away from the airways of the patient).

It is necessary to determine and monitor the pressure within the airways during ventilation (normoventilation), in particular by means of the gas flow reversing elements. This can ensure sufficient ventilation and prevent injury to the airways (e.g. a barotrauma).

A non-negligible pressure loss is caused by way of the gas flow reversing element and by way of the thin catheter/thin lumen, said pressure loss being dependent on numerous variables (applied pressure, volumetric flow rate, diameter of the lumen, length of the lumen, etc.). This pressure loss may have to be taken into account when measuring the pressure of the airways (if the pressure measurement is still effectuated upstream of the gas flow reversing element—i.e. not between the gas flow reversing element and airways).

For the purposes of the pressure measurement, pressure measuring appliances, e.g. manometers, are also connected directly to the lumen, which connects the gas flow reversing element to the airways of the patient, or to the gas flow reversing element itself (by way of example, using the branching piece in the known gas flow reversing elements, i.e. the region of the gas flow reversing element through which respiratory air is supplied and consumed respiratory air is discharged). Here, the pressure measuring appliances continuously have applied thereon the changing pressure conditions in the attached line (lumen/branching piece). Precisely in the case of using gas flow reversing elements, these pressure conditions vary between 0.5 bar and up to 5 bar between each inspiration and expiration process.

These pressure variations may lead to the employed pressure measuring appliances being decalibrated or even destroyed. However, in any case, determining the pressure present in the airways is only possible with great difficulties or it is impossible.

Proceeding therefrom, the object underlying the present invention is that of at least partly overcoming the disadvantages known from the prior art and of developing an arrangement by means of which a simple and reliable pressure measurement can be effectuated. Damage to, or decalibration of, the employed measuring appliances should be prevented.

This object is achieved by an arrangement having the features of patent claim 1. Advantageous developments and configurations of the arrangement are the subject matter of the respectively dependent claims.

The invention relates to an arrangement comprising a switchable connector and a gas flow reversing element which is suitable for exploiting a gas supply under positive pressure, in particular oxygen or another gas suitable for ventilation and/or suitable for the planned treatment, for selectively generating a gas flow from or to a line connector which is connectable to, in particular, airways of a patient by way of a lumen in particular. The gas flow reversing element is embodied at least as a main piece with a branching piece, wherein the main piece connects a pressure connector for connection to the gas supply with at least one closable outlet opening and the branching piece connects, by way of a first line, the main piece to the line connector. A nozzle is embodied and arranged in the main piece in such a way that a gas flow flowing from the pressure connector through the nozzle to the outlet opening also is able to produce a gas flow through the first line in the direction of the outlet opening in the main piece if the outlet opening is open. In particular, use can also be made here of gas flow reversing elements according to WO 2008/113752 A1 or U.S. 61/844,746. The switchable connector is arranged at the branching piece or at the line connector and switchably connects at least a second line to the first line, wherein the switchable connector has at least two switching positions, wherein, (1) in the first switching position, the first line is open and the second line is closed such that the gas flow can flow through the connector in both directions along the first line;

(2) in the second switching position, the second line is flow-connected to the line connector and, in particular, to the lumen via the connector if the switchable connector is arranged at the branching piece or the second line is connected to the lumen if the switchable connector is arranged at the line connector.

In particular, in the second switching position, the first line to the main piece is closed and the second line is flow-connected to the line connector and/or to the lumen (only) via the connector.

In particular, the gas flow reversing element is arranged in an ergonomically shaped housing, which is adapted to a hand of a human, wherein the switchable connector can be transferred at least from the first switching position to the second switching position manually, preferably using at least one finger of the same hand of a human.

Preferably, the connector is actuatable by way of a lever element.

In particular, the lever element is rotatably arranged at the connector for the purposes of actuating the connector.

According to a preferred configuration, the lever element is rotated by substantially a quarter rotation (i.e. through approximately 90 degrees) for a switching process between the first switching position and the second switching position.

In particular, at least one switching process from the second switching position into the first switching position is effectuated automatically. Here, automatically means, in particular, that an actuation of e.g. the lever element is not necessary for this switching process. In particular, restoring elements (e.g. springs or the like) which undertake this switching process are integrated into the connector. In particular, this means that the connector is always arranged in the first switching position in the case of non-actuation.

In particular, the connector is a type of shunt which flow-connects certain lines (in this case a first line to the main piece; a second line, e.g. to the pressure measuring device; and a first line or lumen to the patient) to one another or closes the connection between the lines. In particular, pass-throughs are provided to this end within the connector, with the pass-throughs being able to be connected to the lines attached to the connector, for example by a rotation in different ways (first and second switching position).

Preferably, the connector and the gas flow reversing element are detachably connectable to one another. That is to say, in particular, that the connector and gas flow reversing element are respectively available separately from one another and, for example, connected to one another by way of a so-called "Luer lock" connection.

On the other hand, it is also advantageous if the connector and the gas flow reversing element are connected to one another in a non-detachable (integral; cohesive) manner. That is to say, in particular, that the connector and gas flow reversing element can only be separated from one another by destruction. Such an integral embodiment can, in particular, be handled more easily by a user and may optionally be produced in a more cost-effective manner.

In particular, at least one connection of the group
  connector with the line connector,
  connector with the second line, and
  connector with the first line
is embodied as a so-called "Luer lock" connection.

Further, a method for measuring a pressure in an arrangement according to the invention is proposed, wherein a pressure measuring device (e.g. a manometer) is arranged/connected at the second line, wherein, if the switchable connector is in the second switching position, the pressure in the first line between the connector and the line connector or in the lumen between the connector and, in particular, a patient can be measured by way of the pressure measuring device.

For the safety of the patient, it is important that an inadvertent manipulation on the gas flow reversing element does not already exert any influence on the airways. Therefore, it is advantageous if at least one safety opening is preferably present in the branching piece (see WO 2008/113752 A1). Preferably, there should even be two safety openings, particularly preferably two safety openings that are arranged next to one another or opposite one another. Here, these safety openings at the same time serve to control the positive or negative pressure in the direction of the patient. In the case of a release, they moreover act as pressure equalization openings and facilitate the equalization of an intrathoracic positive or negative pressure if there is a brief pause in the jet ventilation. As a result, the pressure in the lungs can equalize with the external pressure. This is particularly important if the airways are completely obstructed and it is not clear whether the lungs of the patient are too strongly blown up or suctioned empty at the current instant (particularly if there is no pressure measurement at this time or if no pressure measuring device is connected).

When the pressure connector of the gas flow reversing element is connected to a pressurized gas source, a gas flow flows through the nozzle to the outlet opening, leading without safety opening(s) directly to negative pressure at the line connector and hence, possibly, in the airways as well. This is avoided as a result of the safety opening(s) that is/are still open and should have a sufficiently large cross section for this purpose since the negative pressure is equalized there by inflowing ambient air. Negative pressure at the line connector only arises once all safety openings are closed in a targeted manner, for example by the fingers of a human/operator.

Then, a gas or gas mixture flow can also be guided into the airways by additional closing of the outlet opening. By contrast, if the safety openings are released, the gas or gas mixture flow immediately escapes quantitatively into the ambient air. Effective ventilation is obtained by alternately opening and closing the outlet opening in the case of closed safety openings.

In particular, the connector allows the pressure in the airways of a patient (even) to be determined, with the pressure measuring appliance not having strong pressure variations applied thereto.

In particular, the arrangement is designed in such a way that, while in the second switching position, simultaneous closing of outlet opening and of safety openings is prevented or only achievable by deliberate operation.

Preferably, the second line is never flow-connectable to the main piece. This is achieved in that the first line to the main piece is closed in the second switching position and the second line is flow-connected only to the line connector and/or the lumen via the connector.

This ensures, in particular, that the pressure measuring device is not flow-connected to the pressurized gas source. Hence, an application of high pressures (e.g. more than 1.5 bar) will not occur or will only occur if there is a deliberate operation of the arrangement.

Particularly in the case of emergency care, it is advantageous to arrange the outlet opening and the safety openings in such a way that they are closable, selectively on their own or partly or completely together, by hand, preferably with the ball of the hands and/or fingers of only one hand of a human or an operator. Hence, a human is able to carry out, interrupt or, by way of partial closing of the openings, regulate the ventilation as required using one hand, and still has the other hand free for further measures or activities (e.g. securing the catheter or the cannula).

In particular, the safety opening/openings is/are arranged in such a way that they can be operated/closed particularly easily by a specific finger (e.g. by the index finger while the outlet opening is operated/closed by e.g. the thumb). In particular, the same finger which is also used for operating the safety opening must be used for actuating the connector, i.e. for undertaking a switching process. Thus, for the purposes of operating the connector, the finger must be removed from the safety opening. Then, the safety opening is open and the gas flow escapes into the surroundings. This prevents the pressure measuring device from being flow-connected to the pressure of the gas flow from the pressurized gas source.

All that is required for the use of the arrangement according to the invention is a pressurized respiratory gas flask or a stationary pressurized gas connector (e.g. in a hospital) and a connection line.

The explanations in respect of the method are transferable to the arrangement, and vice versa. Preferred exemplary embodiments of the invention are explained in more detail below on the basis of the drawings, with the invention however not being restricted thereto. The same reference signs indicate the same objects. In detail:

Figures 1, 2:
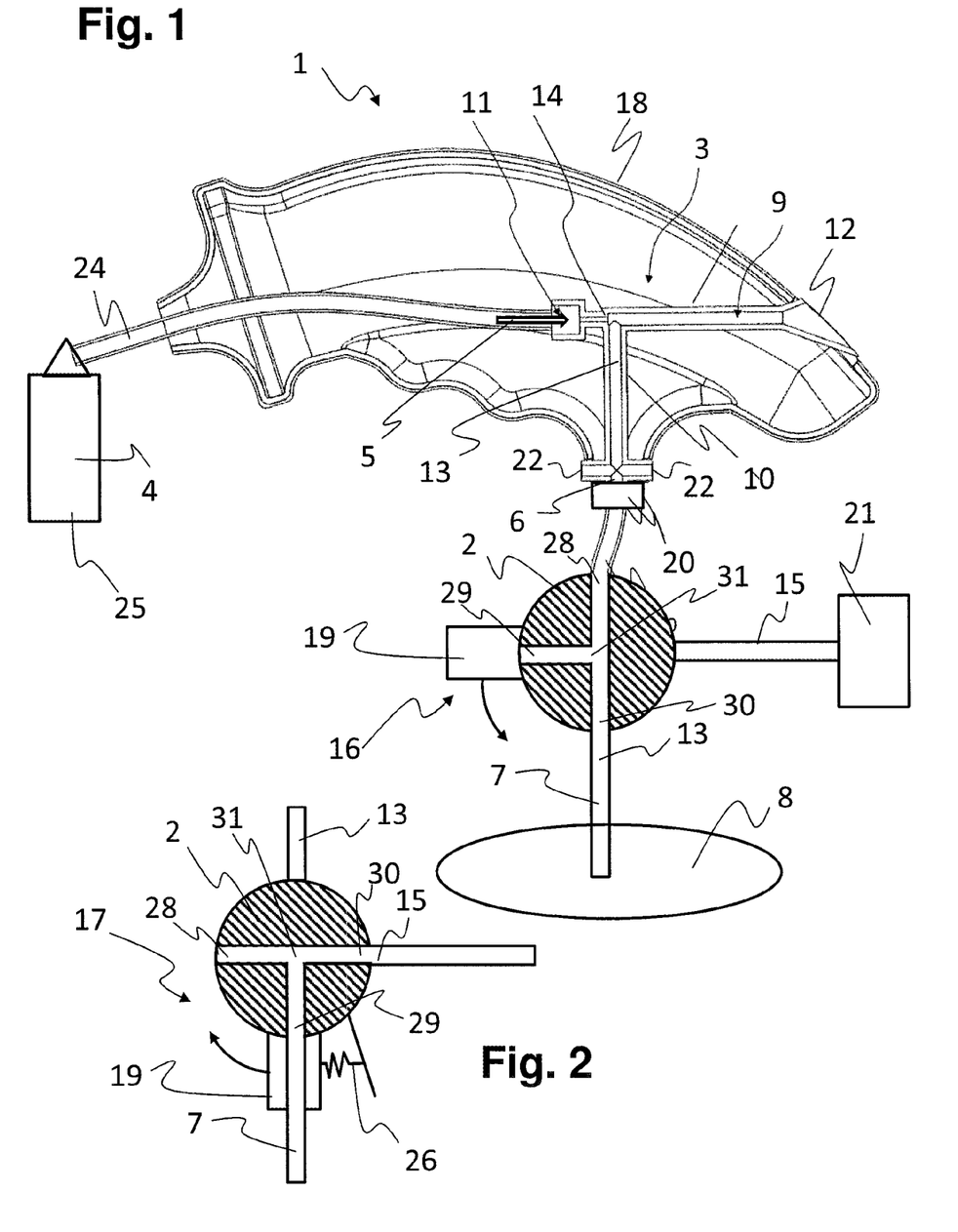
FIG. 1 shows a longitudinal section through an arrangement with schematically illustrated peripheral appliances.
FIG. 2 shows a switchable connector in the second switching position.

FIG. 1 shows a gas flow reversing element 3 with a main piece 9 which connects a pressure connector 11 to an outlet opening 12. The pressure connector 11 can be connected by a connection line 24 to a gas supply 4 under positive pressure in a pressurized gas source 25. In general, an oxygen pressure flask is available for emergency care of patients. The pressurized gas source can also be provided by way of a stationary connector (e.g. in a hospital). A branching piece 10 branches off the main piece 9, said branching piece leading to a line connector 6. A nozzle 14, through which a gas flow 5 can flow from the pressure connector 11 to the outlet opening 12, is formed in the main piece 9, with this nozzle 14 lying in the vicinity of the branching piece 10 such that the gas flow 5 flowing through the nozzle 14 to the outlet opening 12 creates negative pressure in the branching piece 10.

Further, the branching piece 10 has two safety openings 22. For as long as these two safety openings 22 are not closed in a targeted manner, the arrangement 1 has no influence on the airways of a patient 8, even if the gas flow 5 is flowing. Only when these safety openings 22 are closed does negative pressure arise in the branching piece 10 for as long as the outlet opening 12 is open and positive pressure arise if the outlet opening 12 is closed. Preferably, all openings 12, 22 should be arranged in such a way that they can be closed by an operator with one hand in a deliberate manner, but hardly inadvertently. At least the outlet opening 12 should then be closable by one finger (e.g. the thumb) as it must be alternately opened and closed during the ventilation.

Here, the switchable connector is connected to the line connector 6, preferably by way of a so-called "Luer lock" connection 20. The connector 2 and the gas flow reversing element 3 are detachably connected to one another by way of this connection 20.

The whole arrangement 1 is preferably produced from plastic.

Here, the switchable connector 2 is directly arranged at the line connector 6 (between the line connector 6 and the patient 8) on the housing 18 and it connects a second line 15 in a switchable manner to the first line 13, wherein the switchable connector 2 is illustrated here in the first switching position 16. Here, the first line 13 is open and the second line 15 is closed, and so the gas flow 5 can flow through the connector 2 in both directions along the first line 13. A pressure measuring device 21 is connected to the second line 15. A lumen 7 connects the connector 2 and the airways of the patient 8. Here, the connector 2 has a T-shaped connection line 31. The T-shaped connection line 31 extends between a first end 28, a second end 29, and a third end 31. In the shown first switching position 16, the first end 28 is arranged at the line connector 6 and the third end 30 is arranged at the lumen 7, and so a gas flow 5 can flow along the first line 13, through the line connector 6, the connection line 31 and the lumen 7. The second end 29 is closed in this case (e.g. by way of a housing of the connector 2).

The connector 2 is actuatable by way of a lever element 19. The lever element 19 is arranged in rotatable fashion on the connector 2 for the purposes of actuating the connector 2. The lever element 19 is rotated through substantially a quarter rotation (90 degrees) for a switching process between the first switching position 16 and the second switching position 17 (see FIG. 2) (see direction of rotation in FIGS. 1 and 2).

The gas flow reversing element 3 is arranged in an ergonomically shaped housing 18. Here, the housing 18 is shaped in such a way that it is adapted to the human hand. The safety openings 22 can be closed with the fingers; the outlet opening 12 can be wholly or partly closed with the thumb. The connector 2 is arranged in, or, as shown here, in the direct vicinity of, the housing 18 and it can be actuated by way of the lever element 19, in particular using fingers of the same hand. As a result of such a configuration, it is possible to operate the arrangement 1 using only one human hand. It is also possible to provide only one safety opening 22 for the purposes of simplified handling. The housing 18 and the connector 2 can be produced in a manner combined or linked in various ways. What is important is that, in particular, an arrangement 1 that is easily operated manually arises, said arrangement being able to be held in one hand, wherein the outlet opening 12 and the safety openings 22 can be closed with the fingers or with other parts of this hand and wherein the connector 2 is actuatable by way of fingers of the same hand (in particular by the same finger which actuates the safety opening 22).

FIG. 2 shows a switchable connector 2 in the second switching position 17. The connector 2 has a restoring device 26 (e.g. a compression spring) such that the switching process from the second switching position 17 back into the first switching position 16 is effectuated automatically. In the second switching position 17 shown here, the second line 15 is flow-connected via the third end 30, the connection line 31, and the second end 29 of the connector 2 only to the lumen 7 such that the pressure measuring device 21 can measure the pressure in the lumen 7 and hence the pressure in the airways of a patient 8 is determinable. In the second switching position 17 shown here, the connector 2 only connects the second line 15 to the lumen 7. Here, the first end 28 is closed (e.g. by way of a housing of the connector 2).

Shown here is that the connector 2 in the second switching position 17 closes the first line 13 to the main piece 9 and the second line 15 is only flow-connected to the lumen 7 by the connector 2.

Alternatively, it is possible to integrate the connector 2 into the housing 18 of the gas flow reversing element 3. Then, for example, the switchable connector 2 is arranged at the branching piece 10, i.e. attached to the first line 13 between the main piece 3 and line connector 6 (for a lumen 7, e.g. a catheter). The first line 13 is opened or closed by the connector 2, with the second line 15 being connectable via the first line 13 and the line connector 6 to the lumen 7.

Figure 3:
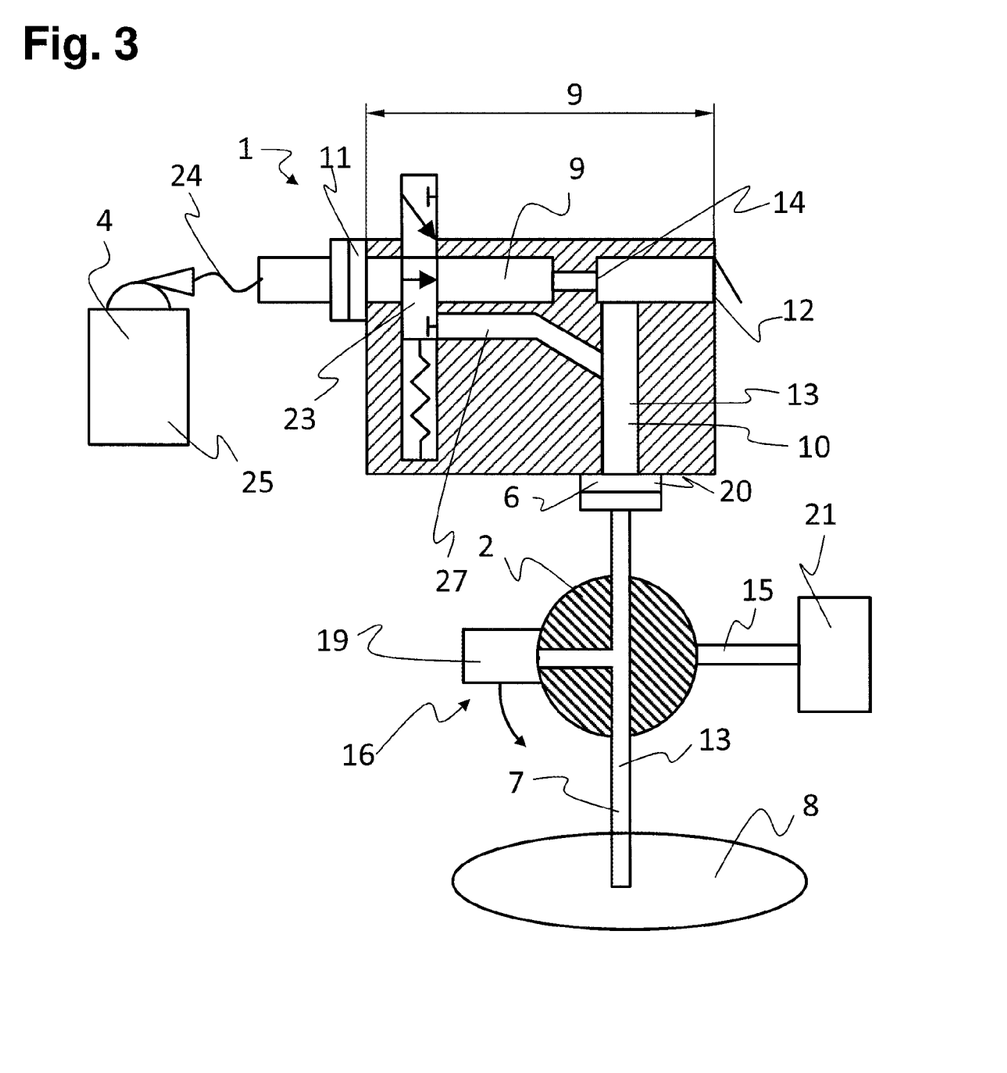
FIG. 3 schematically shows a section of an arrangement.

FIG. 3 schematically shows a section of an arrangement 1. This arrangement 1 comprises a gas flow reversing element 3, e.g. according to U.S. 61/844,746. Here, a gas supply 4 under positive pressure is likewise used for alternate production of a gas flow 5 from or to the line connector 6. The gas flow reversing element 3 comprises a main piece 9 with a branching piece 10, with the main piece 9 connecting a pressure connector 11 for connection with the gas supply 4 to at least one closable outlet opening 12 and the branching piece 10 connecting the main piece 9 to the line connector 6 by way of a first line 13. In the main piece 9, a nozzle 14 is embodied and arranged in such a way that a gas flow 5 through the first line 13 is producible in the direction of the outlet opening 12 by a gas flow 5 in the main piece 9 flowing from the pressure connector 11 through the nozzle 14 to the outlet opening 12 when the outlet opening 12 is open. Here, a closing element 23 (e.g. a switchable valve or a clamp which can press together and close a flexible line from the outside) is arranged in the main piece 9 such that the nozzle 14 can optionally be circumvented and the gas flow 5 can be directly supplied to the line connector 6 via the bypass 27. Here too, the switchable connector 2 is arranged at the line connector 6 and at least one second line 15 is switchably connectable to the first line 13.

Figure 4:
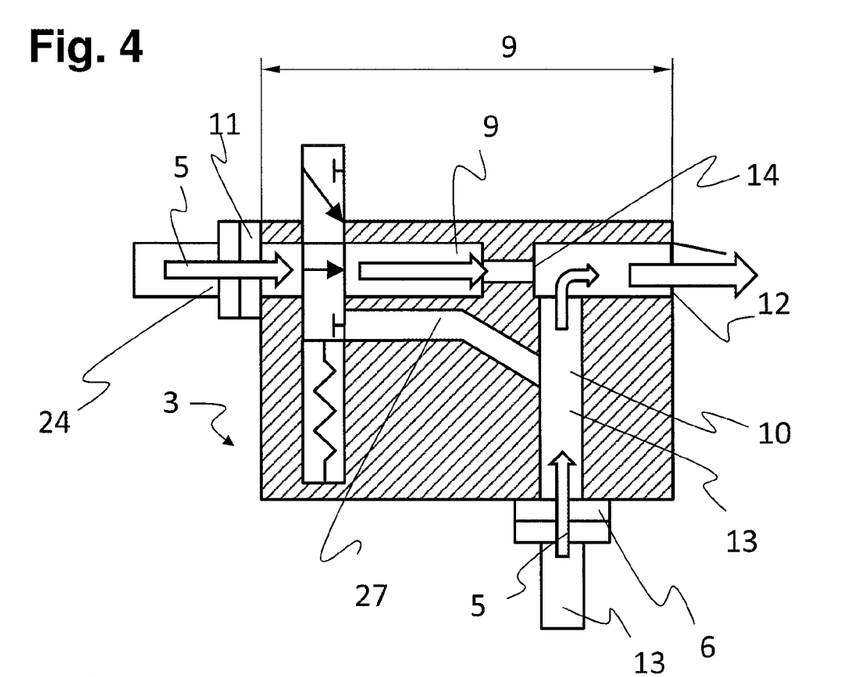
FIG. 4 schematically shows a section of a gas flow reversing element with a bypass.

FIG. 4 schematically shows a section of a gas flow reversing element 3 with a bypass 27 (e.g. according to U.S. 61/844,746, and according to FIG. 3). As a result of actuating the closing element 23, the gas flow 5 in this case flows from the pressure connector 11 in the direction of the outlet opening 12 and hence produces a further gas flow 5, which flows via the line connector 6 through the branching piece 10 to the outlet opening 12.

Figure 5:
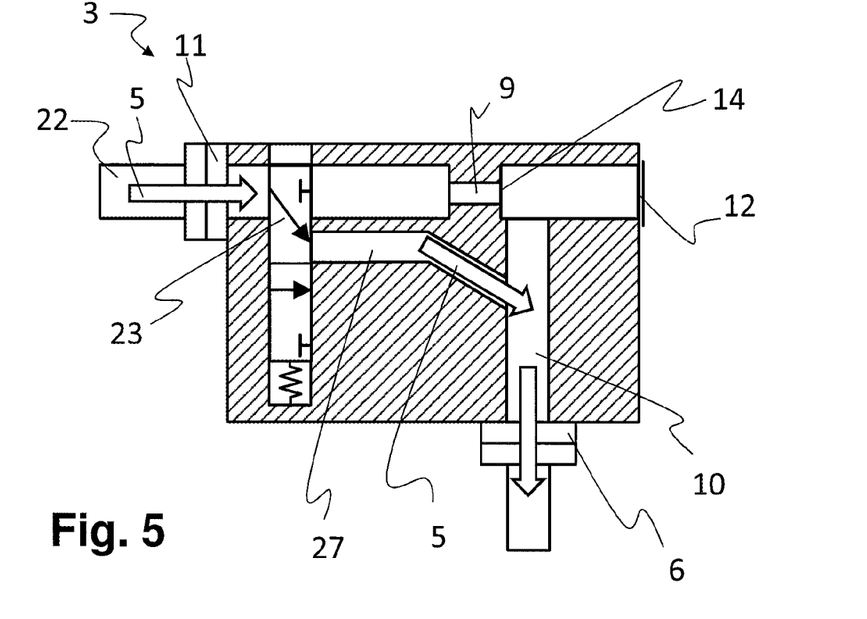
FIG. 5 schematically shows a section of the gas flow reversing element of FIG. 4 in another position of the closing element.

FIG. 5 schematically shows a section of the gas flow reversing element 3 from FIG. 4 with another position of the closing element 23. Here the gas flow 5, which flows into the gas flow reversing element 3 via the pressure connector 11, is transferred via the bypass 27 directly into the first line 13 in the branching piece 10, without a pressure loss occurring as a result of flowing over the nozzle 14.

Figure 6:
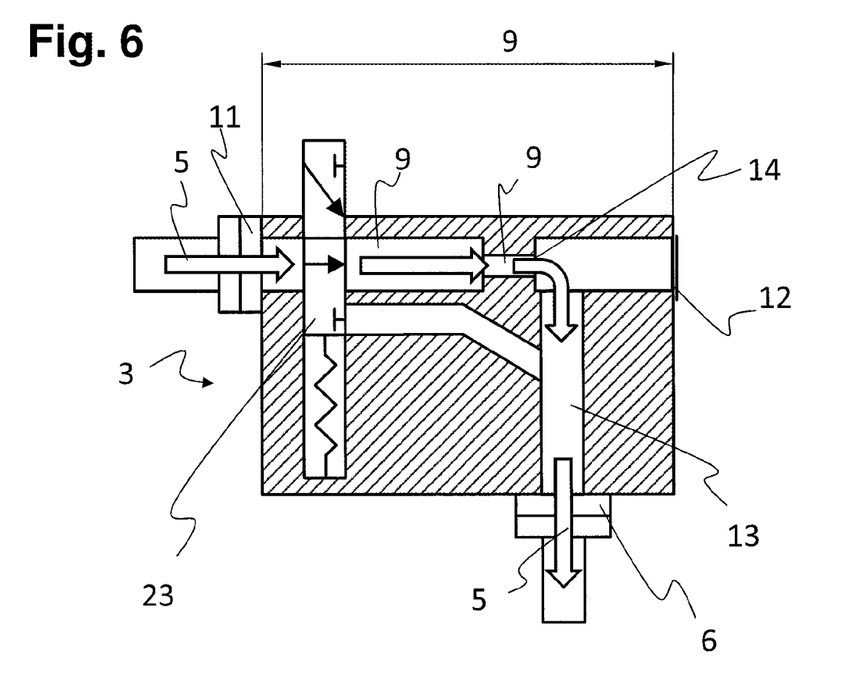
FIG. 6 schematically shows a section of the gas flow reversing element of FIGS. 4 and 5 with a further position of the closing element and a closed outlet opening.

FIG. 6 schematically shows a section of the gas flow reversing element 3 from FIGS. 4 and 5 in a further position of the closing element 23 and with a closed outlet opening 12. Here, the gas flow 5, which flows into the gas flow reversing element 3 via the pressure connector 11, is transferred via the main piece 9 and the nozzle 14 into the first line 13 in the branching piece 10.

LIST OF REFERENCE SIGNS

1 Arrangement
2 Connector
3 Gas flow reversing element
4 Gas supply
5 Gas flow
6 Line connector
7 Lumen
8 Patient
9 Main piece
10 Branching piece
11 Pressure connector
12 Outlet opening
13 First line
14 Nozzle
15 Second line
16 First switching position
17 Second switching position
18 Housing
19 Lever element
20 Connection
21 Pressure measuring device
22 Safety opening
23 Closing element
24 Connection line
25 Pressurized gas source
26 Restoring device
27 Bypass
28 First end
29 Second end
30 Third end
31 Connection line

The invention claimed is:

1. An arrangement comprising a switchable connector, a restoring device to automatically return the switchable connector from a second switching position to a first switching position, and a gas flow reversing element which is suitable for exploiting a gas supply under positive pressure for selectively generating a gas flow from or to a line connector which is connectable to airways of a patient by way of a lumen; wherein the gas flow reversing element is embodied at least as a main piece with a branching piece, wherein the main piece connects a pressure connector for connection to the gas supply with at least one closable outlet opening and the branching piece connects, by way of a first line, the main piece to the line connector, wherein a nozzle is embodied and arranged in the main piece in such a way that a gas flow flowing from the pressure connector through the nozzle to the outlet opening also is able to produce a gas flow through the first line in the direction of the outlet opening in the main piece if the outlet opening is open, wherein the switchable connector is arranged at the line connector and switchably connects at least to a second line or to the first line, wherein the switchable connector has at least two switching positions, wherein, in the first switching position, the first line is open and the second line is closed such that the gas flow can flow through the switchable connector in both directions along the first line to the line connector;

in the second switching position, upon actuatable rotation of the switchable connector, the first line to the main piece is closed and the second line is flow-connected to the lumen via the switchable connector, wherein in the second switching position the is configured to cause causes automatic return of the switchable connector to the first switching position when actuation force is no longer applied to the switchable connector wherein, in the second switching position, the first line to the main piece is closed and the second line is flow-connected to the lumen via the switchable connector connectable to the airways of the patient, so that at no point in time the second line is flow-connectable to the main piece.

2. The arrangement as claimed in claim 1, wherein the gas flow reversing element is arranged in an ergonomically shaped housing, which is adapted to a hand of a human, wherein the switchable connector is configured to be transferred at least from the first switching position to the second switching position manually.

3. The arrangement as claimed in claim 1, wherein the switchable connector is actuatable by way of a lever element.

4. The arrangement as claimed in claim 3, wherein the lever element is rotatably arranged at the switchable connector for the purposes of actuating the switchable connector.

5. The arrangement as claimed in claim 4, wherein the lever element is rotated by substantially a quarter rotation for a switching process between the first switching position and the second switching position.

6. The arrangement as claimed in claim 1, wherein the line connector and the gas flow reversing element are detachably connectable to one another.

7. The arrangement as claimed in claim 1, wherein the line connector and the gas flow reversing element are connected to one another in a non-detachable manner.

8. The arrangement as claimed in claim 1, wherein a connection between the first line and the switchable connector, or between the second line and the switchable connector, or between both the first line and second line to the switchable connector is embodied as a Luer-lock connection.

9. A method for measuring a pressure in an arrangement as claimed in claim 1, wherein a pressure measuring device is arranged at the second line, wherein, if the switchable connector is in the second switching position, the pressure in the first line between the patient and the line connector or in the lumen between the switchable connector and the patient can be measured by way of the pressure measuring device.

10. The arrangement as claimed in claim 2, wherein the switchable connector configured to be transferred at least from the first switching position to the second switching position manually is configured to be transferred from at least the first switching position to the second switching position using at least one finger of the same hand of a human.

11. The arrangement as claimed in claim 1, wherein the restoring device comprises a spring that is configured to push against a rotatable lever actuating the switchable connector.

12. The arrangement as claimed in claim 1, wherein the switchable connector comprises a rotatable T-shaped line.

* * * * *